US010771887B2

(12) United States Patent
Bao et al.

(10) Patent No.: US 10,771,887 B2
(45) Date of Patent: Sep. 8, 2020

(54) ANISOTROPIC BACKGROUND AUDIO SIGNAL CONTROL

(71) Applicant: Cisco Technology, Inc., San Jose, CA (US)

(72) Inventors: Feng Bao, Sunnyvale, CA (US); David William Nolan Robison, Campbell, CA (US); Jian Zou, Shanghai (CN); Tor Sundsbarm, San Jose, CA (US)

(73) Assignee: CISCO TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 16/229,693

(22) Filed: Dec. 21, 2018

(65) Prior Publication Data

US 2020/0204902 A1 Jun. 25, 2020

(51) Int. Cl.

| | |
|---|---|
| ***A61F 11/06*** | (2006.01) |
| ***H04R 1/10*** | (2006.01) |
| ***H04R 3/02*** | (2006.01) |
| ***H04R 3/04*** | (2006.01) |

(52) U.S. Cl.

CPC ............. *H04R 1/1083* (2013.01); *H04R 3/02* (2013.01); *H04R 3/04* (2013.01); *H04R 2410/05* (2013.01)

(58) Field of Classification Search

CPC ....................................................... A61F 11/06

See application file for complete search history.

(56) References Cited

U.S. PATENT DOCUMENTS

| | | | | |
|---|---|---|---|---|
| 5,748,725 A * | 5/1998 | Kubo | H04R 3/005 379/392.01 |
| 6,009,184 A | 12/1999 | Tate et al. | |
| 6,978,010 B1 * | 12/2005 | Short | H04M 1/6008 379/388.03 |
| 7,773,759 B2 | 8/2010 | Alves et al. | |
| 8,081,780 B2 | 12/2011 | Goldstein et al. | |
| 8,473,287 B2 * | 6/2013 | Every | G10L 21/0208 704/226 |
| 8,660,281 B2 | 2/2014 | Bouchard et al. | |

(Continued)

OTHER PUBLICATIONS

Sean U.N. Wood et al., "Blind Speech Separation and Enhancement With GCC-NMF", IEEE/ACM Transactions on Audio, Speech, and Language Processing, vol. 25, No. 4, Apr. 2017, 11 pages.

(Continued)

*Primary Examiner* — Olisa Anwah

(74) *Attorney, Agent, or Firm* — Edell, Shapiro & Finnan, LLC

(57) ABSTRACT

In one example, a headset obtains, from a first microphone on the headset, a first audio signal including a user audio signal and an anisotropic background audio signal. The headset obtains, from a second microphone on the headset, a second audio signal including the user audio signal and the anisotropic background audio signal. The headset extracts, from the first audio signal and the second audio signal, using a first adaptive filter, a reference audio signal including the anisotropic background audio signal. Based on the reference signal, the headset cancels, using a second adaptive filter, the anisotropic background audio signal from a third audio signal derived from the first and second audio signals to produce an output audio signal. The headset provides the output audio signal to a receiver device.

20 Claims, 9 Drawing Sheets

(56) References Cited

U.S. PATENT DOCUMENTS

| | | | | |
|---|---|---|---|---|
| 9,685,171 | B1 * | 6/2017 | Yang | G10L 21/0208 |
| 10,079,026 | B1 | 9/2018 | Ebenezer | |
| 10,297,267 | B2 * | 5/2019 | Ebenezer | H04R 1/406 |
| 10,455,319 | B1 * | 10/2019 | Wu | H04R 1/222 |
| 2007/0274552 | A1 * | 11/2007 | Konchitsky | H04R 3/007<br>381/328 |
| 2010/0022283 | A1 * | 1/2010 | Terlizzi | H04M 1/05<br>455/570 |
| 2011/0130176 | A1 * | 6/2011 | Magrath | G10K 11/178<br>455/570 |
| 2014/0270194 | A1 * | 9/2014 | Des Jardins | G10L 21/0224<br>381/56 |
| 2016/0105755 | A1 * | 4/2016 | Olsson | G10L 21/0216<br>381/71.6 |
| 2017/0006372 | A1 * | 1/2017 | Yang | H04R 1/1083 |
| 2017/0236528 | A1 * | 8/2017 | Lepauloux | G10L 21/0264<br>704/233 |
| 2018/0091882 | A1 * | 3/2018 | Christiansen | H04R 1/083 |
| 2018/0122400 | A1 * | 5/2018 | Rasmussen | G10K 11/002 |
| 2018/0174597 | A1 * | 6/2018 | Lee | H04R 29/005 |

OTHER PUBLICATIONS

Vocal Technologies, Ltd., "Adaptive Noise Reduction", https://www.vocal.com/noise-reduction/adaptive-noise-reduction/, Feb. 27, 2017, 2 pages.

* cited by examiner

200A

200B

ANISOTROPIC BACKGROUND AUDIO SIGNAL CONTROL

TECHNICAL FIELD

The present disclosure relates to audio signal control.

BACKGROUND

Local participants in conferencing sessions (e.g., online or web-based meetings) often use headsets with an integrated speaker and/or microphone to communicate with remote meeting participants. The microphone detects speech from the local participant for transmission to the remote meeting participants, but frequently picks up undesired anisotropic background audio signals (e.g., background talkers) along with the speech. When transmitted with the speech, the undesired anisotropic background audio signals can prevent the remote meeting participants from understanding the speech. This can be a hindrance to all meeting participants and reduce the effectiveness of the conferencing session.

DESCRIPTION OF EXAMPLE EMBODIMENTS

Overview

In one example embodiment, a headset obtains, from a first microphone on the headset, a first audio signal including a user audio signal and an anisotropic background audio signal. The headset obtains, from a second microphone on the headset, a second audio signal including the user audio signal and the anisotropic background audio signal. The headset extracts, from the first audio signal and the second audio signal, using a first adaptive filter, a reference audio signal including the anisotropic background audio signal.

Based on the reference signal, the headset cancels, using a second adaptive filter, the anisotropic background audio signal from a third audio signal derived from the first and second audio signals to produce an output audio signal. The headset provides the output audio signal to a receiver device.

EXAMPLE EMBODIMENTS

Figure 1:
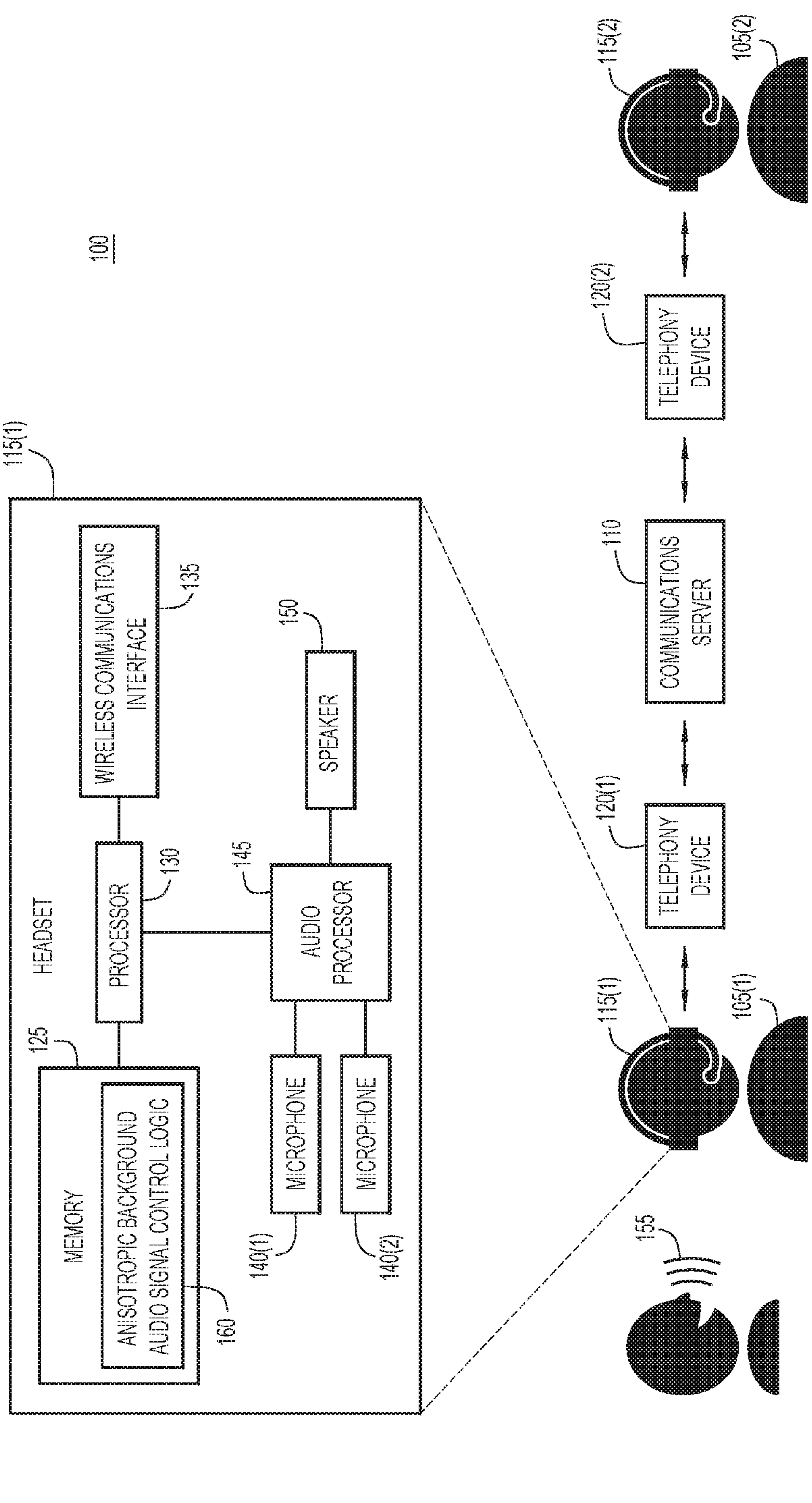
FIG. 1 illustrates a system for controlling an anisotropic background audio signal, according to an example embodiment.

With reference made to FIG. 1, shown is an example system 100 for controlling an anisotropic background audio signal. In the scenario depicted by FIG. 1, meeting attendees 105(1) and 105(2) are attending an online/remote meeting (e.g., audio call) or conference session. System 100 includes communications server 110, headsets 115(1) and 115(2), and telephony devices 120(1) and 120(2). Communications server 110 is configured to host or otherwise facilitate the meeting. Meeting attendee 105(1) is wearing headset 115(1) and meeting attendee 105(1) is wearing headset 115(2). Headsets 115(1) and 115(2) enable meeting attendees 105(1) and 105(2) to communicate with (e.g., speak and/or listen to) each other in the meeting. Headsets 115(1) and 115(2) may pair to telephony devices 120(1) and 120(2) to enable communication with communications server 110. Examples of telephony devices 120(1) and 120(2) may include desk phones, laptops, conference endpoints, etc.

FIG. 1 shows a block diagram of headset 115(1). Headset 115(1) includes memory 125, processor 130, and wireless communications interface 135. Memory 125 may be read only memory (ROM), random access memory (RAM), magnetic disk storage media devices, optical storage media devices, flash memory devices, electrical, optical, or other physical/tangible memory storage devices. Thus, in general, memory 125 may comprise one or more tangible (non-transitory) computer readable storage media (e.g., a memory device) encoded with software comprising computer executable instructions and when the software is executed (by the processor 130) it is operable to perform the operations described herein.

Wireless communications interface 135 may be configured to operate in accordance with the Bluetooth® short-range wireless communication technology or any other suitable technology now known or hereinafter developed. Wireless communications interface 135 may enable communication with telephony device 120(1). Although wireless communications interface 135 is shown in FIG. 1, it will be appreciated that other communication interfaces may be utilized additionally/alternatively. For example, in another embodiment, headset 115(1) may utilize a wired communication interface to connect to telephony device 120(1).

Headset 115(1) also includes microphones 140(1) and 140(2), audio processor 145, and speaker 150. Audio processor 145 may include one or more integrated circuits that convert audio detected by microphones 140(1) and 140(2) to digital signals that are supplied (e.g., as receive signals) to the processor 130 for wireless transmission via wireless communications interface 135 (e.g., when meeting attendee 105(1) speaks). Thus, processor 130 is coupled to receive signals derived from outputs of microphones 140(1) and 140(2) via audio processor 145. Audio processor 145 may also convert received audio (via wireless communication interface 135) to analog signals to drive speaker 150 (e.g., when meeting attendee 105(2) speaks). Headset 115(2) may include similar functional components as those shown at 120 with reference to headset 115(1).

Anisotropic background audio signal 155 is present in the local environment of headset 115(1). In this example, anisotropic background audio signal 155 originates from person who is loudly speaking near meeting attendee 105(1), although it will be appreciated that anisotropic background audio signal 155 may be any noise that reaches microphones 140(1) and 140(2) at different levels of magnitude. Here, because the person is standing to one side of meeting attendee 105(1), the noise from the person reaches microphone 140(1) at a different (e.g., lower) level of magnitude than at microphone 140(2).

Conventionally, anisotropic background audio signal 155 would heavily interfere with the online meeting between meeting attendees 105(1) and 105(2). For example, in some conventional headsets, the anisotropic background audio signal 155 would drown out any speech from meeting attendee 105(1). Other conventional headsets might be configured for traditional noise reduction or suppression, although these are too limited to adequately deal with anisotropic background audio signal 155. Traditional noise reduction algorithms might not suppress anisotropic background audio signal 155 because anisotropic background audio signal 155 is a speech signal. Moreover, traditional noise suppression algorithms can attempt to suppress the anisotropic background audio signal 155 at some frequency and time, but this often distorts the speech from meeting attendee 105(1) because that speech and the anisotropic background audio signal 155 generally have some overlap in time and frequency. Thus, traditional methods often fail because the anisotropic background audio signal 155 and the speech from meeting attendee 105(1) can have similar energy signals.

Accordingly, in order to alleviate noise interference due to anisotropic background audio signal 155, anisotropic background audio signal control logic 160 is provided in memory 125. Briefly, anisotropic background audio signal control logic 160 causes processor 130 to perform operations to cancel (rather than merely reduce or suppress by conventional means) anisotropic background audio signal 155. Anisotropic background audio signal control logic 160 enables headset 115(1) to cancel anisotropic background audio signal 155 without distorting speech from meeting attendee 105(1). Headset 115(1) may remove anisotropic background audio signal 155 before providing an output audio signal to headset 115(2). It will be appreciated that at least a portion of anisotropic background audio signal control logic 160 may be included in devices other than headset 115(1), such as at communications server 110.

Figure 2A:
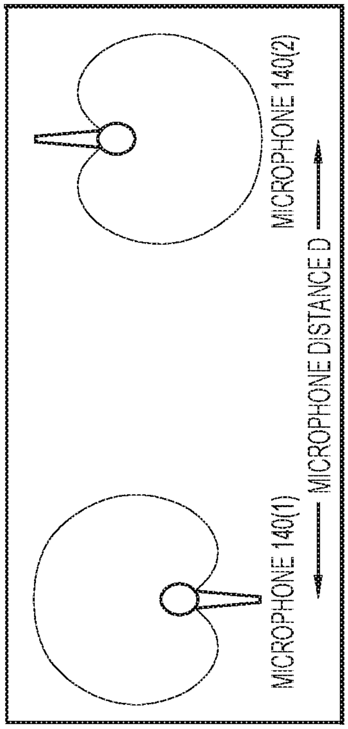
FIGS. 2A and 2B illustrate respective arrangements of microphones employed in a headset with a boom, according to an example embodiment.
Figure 2B:
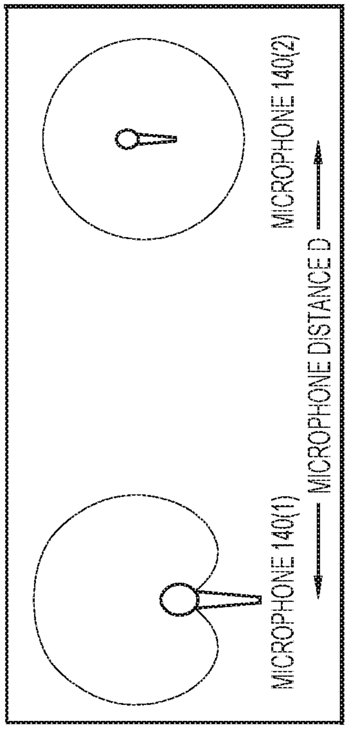

Headset 115(1) may have a boom design or a boomless design. In a boom design, headset 115(1) includes a boom that houses microphones 140(1) and 140(2). FIGS. 2A and 2B respectively illustrate example arrangements 200A and 200B of microphones 140(1) and 140(2) employed in headset 115(1) with a boom. In both arrangements 200A and 200B, microphones 140(1) and 140(2) are separated by a distance D. Distance D may vary depending on the specific use case, but may be large enough to enable implementation of the techniques described herein. Furthermore, in both arrangements 200A and 200B, microphone 140(1) is a directional microphone oriented toward a source of a user audio signal (e.g., the mouth of meeting attendee 105(1)). In arrangement 200A, microphone 140(2) is a directional microphone oriented away from the source of the user audio signal. In arrangement 200B, microphone 140(2) is an omnidirectional microphone.

In a boomless design, headset 115(1) includes a first earpiece that houses microphone 140(1) and a second earpiece that houses microphone 140(1). One of the first and second earpieces may be configured for the left ear of meeting attendee 105(1), and the other of the first and second earpieces may be configured for the right ear of meeting attendee 105(1). Microphones 140(1) and 140(2) may both be oriented toward the source of the user audio signal, and may be unidirectional or omnidirectional. It will be appreciated that microphones 140(1) and 140(2) may be physical microphones or virtual microphones comprising an array of physical microphones. In either design, the relative position between microphones 140(1) and 140(2) and the mouth of meeting attendee 105(1) does not change. Moreover the distances between the mouth and microphones 140(1) and 140(2) are relatively short, and therefore audio signals from the direct acoustic path tend to dominate.

Figure 3:
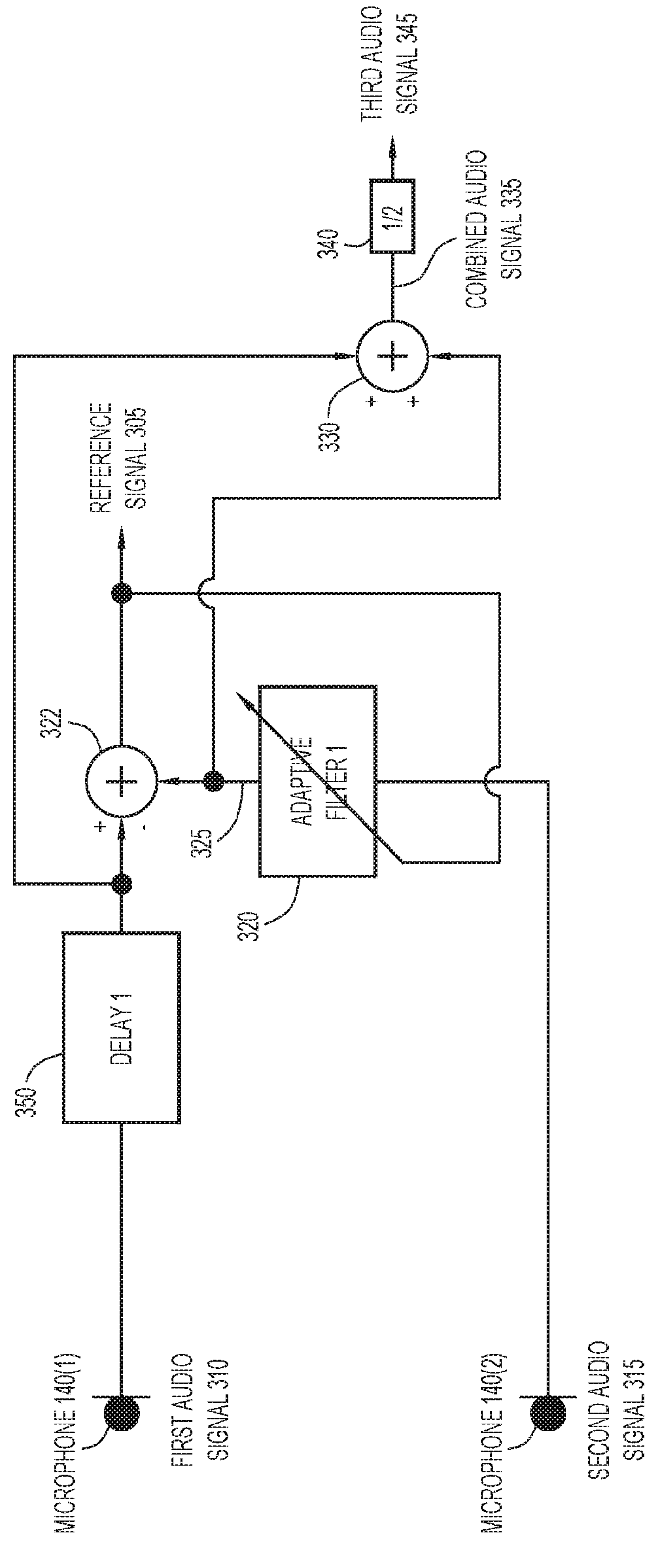
FIG. 3 is a functional signal processing flow diagram illustrating extraction of a reference signal that includes an anisotropic background audio signal, according to an example embodiment.

FIG. 3 is an example functional signal processing flow diagram 300 illustrating extraction of a reference audio signal 305 that includes anisotropic background audio signal 155. Reference is also made to FIG. 1 for purposes of the description of FIG. 3. Headset 115(1) obtains, from microphone 140(1), a first audio signal 310 including a user audio signal (e.g., speech from meeting attendee 105(1)) and anisotropic background audio signal 155. Headset 115(1) further obtains, from microphone 140(2), a second audio signal 315 including the user audio signal and anisotropic background audio signal 155. In other words, first audio signal 310 and second audio signal 315 both include the (desired) user audio signal and the (undesired) anisotropic background audio signal 155. In this example, the relative magnitude of anisotropic background audio signal 155 is greater at microphone 140(2), and the relative magnitude of the user audio signal is greater at microphone 140(1). As such, first audio signal 310 includes a stronger user audio signal, and second audio signal 315 includes a stronger anisotropic background audio signal 155.

Headset 115(1) extracts, from first audio signal 310 and second audio signal 315, reference audio signal 305. Reference signal 305 may include anisotropic background audio signal 155 and any (isotropic) background noise, but may exclude most or all of the user audio signal. Headset 115(1) uses adaptive filter 320 (e.g., time domain element filter) to extract the reference audio signal 305. In this example, first audio signal 310 is the primary input for adaptive filter 320, second audio signal 315 is the reference input for adaptive filter 320, and reference signal 305 is the error output of adaptive filter 320. Adder 322 generates reference signal 305 based on an output signal 325 of adaptive filter 320 and first audio signal 310 (e.g., by subtracting output signal 325 from first audio signal 310).

As shown in FIG. 3, in a boomless design, adder 330 may combine output signal 325 with first audio signal 310 to produce a combined signal 335. Scaling node 340 may scale the combined signal by one-half to produce third audio signal 345. Thus, third audio signal 345 may include an enhanced user audio signal. In a boom design (not shown), the first audio signal 310 may be used as reference signal 305 because microphone 140(1) picks up the user audio signal better than microphone 140(2).

In one example, delay node 350 may delay the first audio signal 310 by a length of time equal to a difference between a time at which the user audio signal reaches microphone 140(1) and a time at which the user audio signal reaches microphone 140(2). Delaying the first audio signal 310 may ensure that adaptive filter 320 converges when the user audio signal is present. The length of time may correspond to distance D (FIG. 2) and the way in which meeting attendee 105(1) is wearing headset 115(1). For example, in a boomless design, meeting attendee 105(1) may place the left or right earpiece relatively far forward or backward such that the user audio signal reaches the left and right earpieces at different times. In this example, the length of time of the delay may be the maximum possible time difference at which the user audio signal reaches the left and right earpieces. The delay may be on the order of hundreds of microseconds. The tail length of adaptive filter 320 may approximately double the delay, and may be less than one millisecond.

Figure 4:
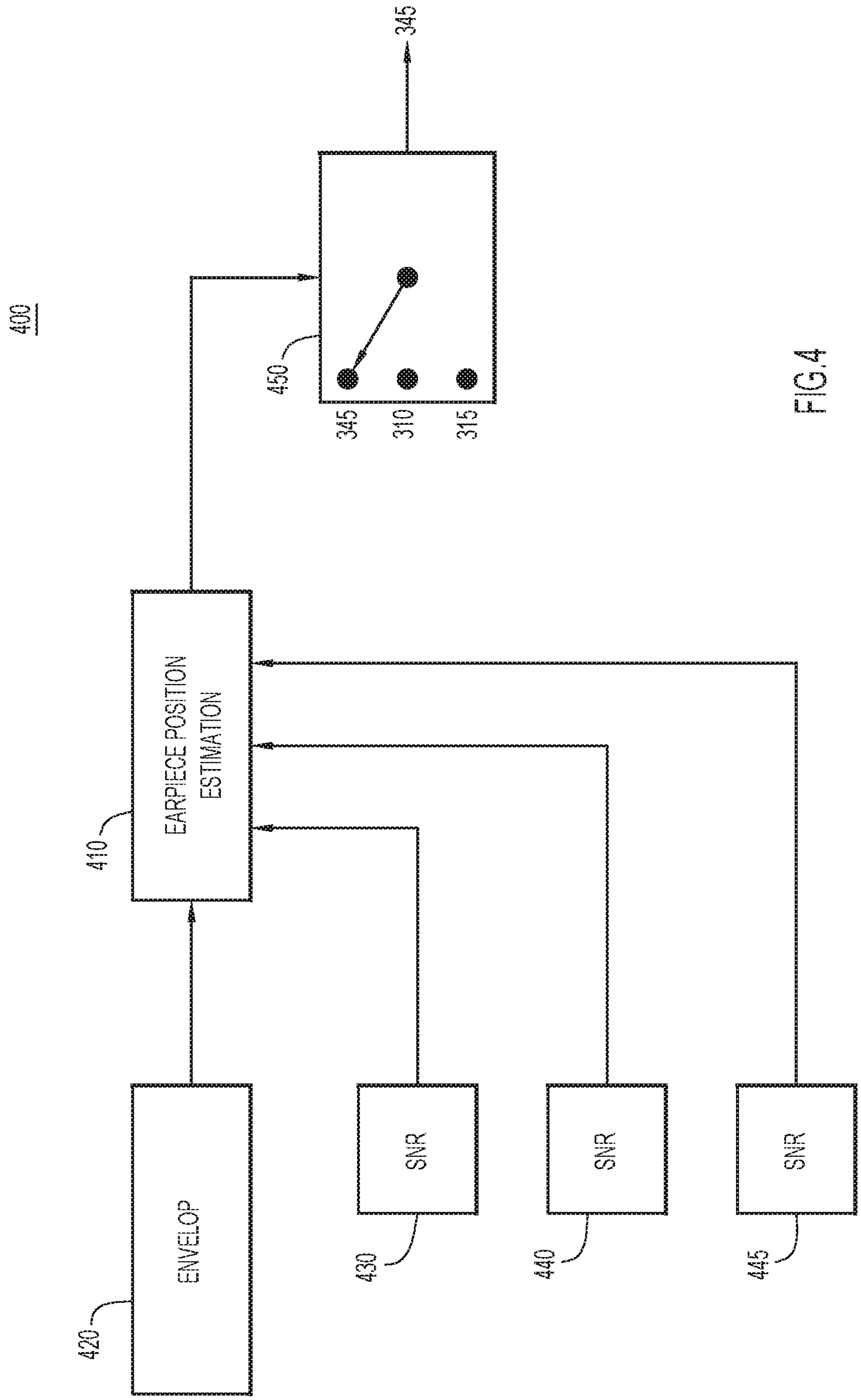
FIG. 4 is a functional signal processing flow diagram illustrating signal selection based on headset position, according to an example embodiment.

FIG. 4 is an example functional signal processing flow diagram 400 illustrating signal selection based on headset position. Reference is also made to FIGS. 1 and 3 for purposes of the description of FIG. 4. The anisotropic background audio signal control logic 160 of headset 115(1) may include earpiece position estimation function 410, which estimates earpiece position on meeting attendee 105 (1). Earpiece position estimation function 410 may perform earpiece position estimation based on the envelop 420 of adaptive filter 320, Signal-to-Noise Ratio (SNR) 430 of first audio signal 310, SNR 440 of second audio signal 315, and SNR 445 of third audio signal 345. Envelope 420 (e.g., in the time domain) may provide a strong indication of earpiece position. In an ideal case, the user audio signal reaches the left and right earpieces at the same time, meaning that adaptive filter 320 should have only one peak (at the delay of delay node 350) with the other taps at almost zero. When the earpieces are not in the correct position, envelop 420 may include other peaks. In the non-ideal case, envelop 420, along with SNRs 430, 440, and 445, may be used to determine earpiece position estimation. When earpiece position estimation function 410 indicates that the earpieces are not ideally positioned, one of the first audio signal 310, second audio signal 315, and third audio signal 345 having the highest SNR may be selected.

Thus, first audio signal 310, second audio signal 315, and third audio signal 345 are candidate audio signals. Based on earpiece position estimation function 410, candidate signal selection function 450 selects one of the candidate audio signals (here, third audio signal 345). Candidate signal selection function 450 may make the selection based on SNRs 430, 440, and/or 445 (e.g., by selecting the highest SNR), and/or based on envelop 420. For example, in a boomless design, when meeting attendee 105(1) has not placed the earpieces at the optimal positions, the signal from one of microphones 140(1) and 140(2) may have a significantly lower level of the user audio signal than the other of microphones 140(1) and 140(2). Accordingly, in certain situations it may be preferable to intelligently select a signal with the highest SNR instead of, for example, the third audio signal 345.

Figure 5:
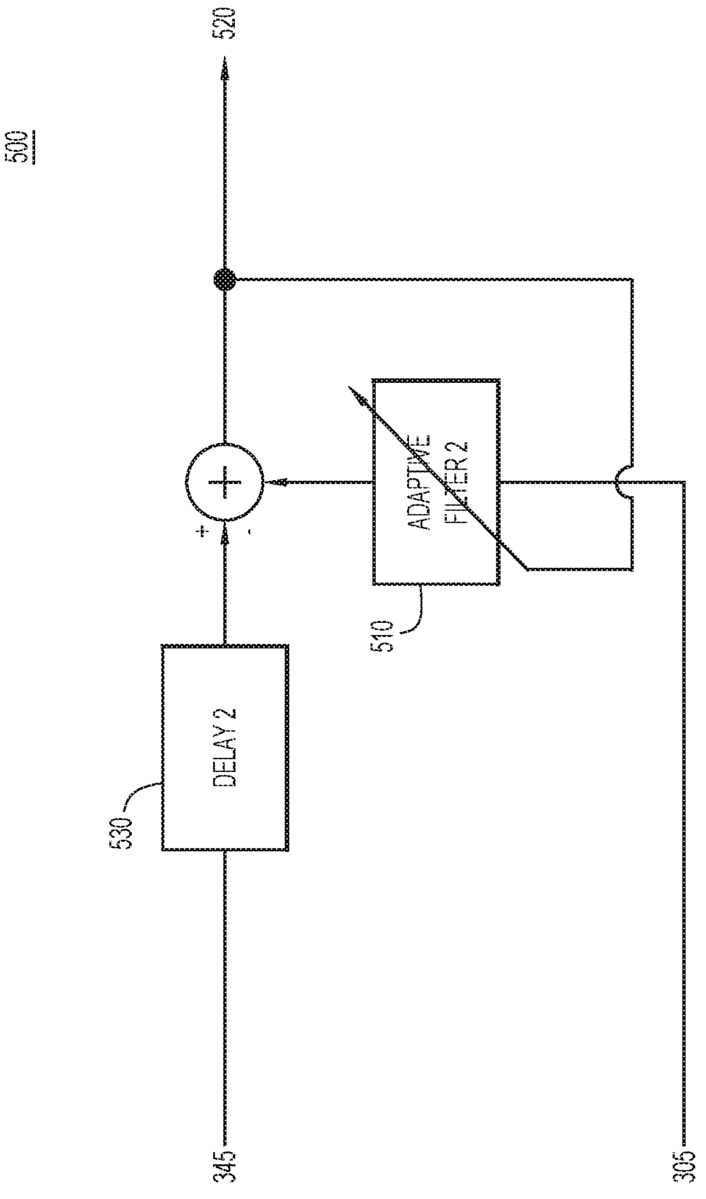
FIG. 5 is a functional signal processing flow diagram illustrating cancellation of an anisotropic background audio signal, according to an example embodiment.

FIG. 5 is an example functional signal processing flow diagram 500 illustrating cancellation of anisotropic background audio signal 155. Reference is also made to FIGS. 1, 3 and 4 for purposes of the description of FIG. 5. The anisotropic background audio signal control logic 160 of headset 115(1) may use adaptive filter 510 to cancel anisotropic background audio signal 155 from the third audio signal 345 based on reference signal 305. The third audio signal 345, having been selected by candidate signal selection function 450, is the primary input for adaptive filter 510. Reference signal 305 is the reference input for adaptive filter 510. Fourth audio signal 520 is the error output of adaptive filter 510. Delay node 530 may delay the third audio signal 345 to ensure that adaptive filter 510 converges.

Because adaptive filter 320 (FIG. 3) already removed the user audio signal from reference signal 305, adaptive filter 510 may not distort the user audio signal in the third audio signal 345. Adaptive filter 510 may be a time or frequency domain element filter, although a frequency domain implementation may be particularly computation efficient. The tail length of adaptive filter 510 may be in the range of 10 to 50 milliseconds, since the anisotropic background audio signal 155 received by microphones 140(1) and 140(2) may have reflections due to the acoustic environment (e.g., the head of meeting attendee 105(1)).

Figure 6:
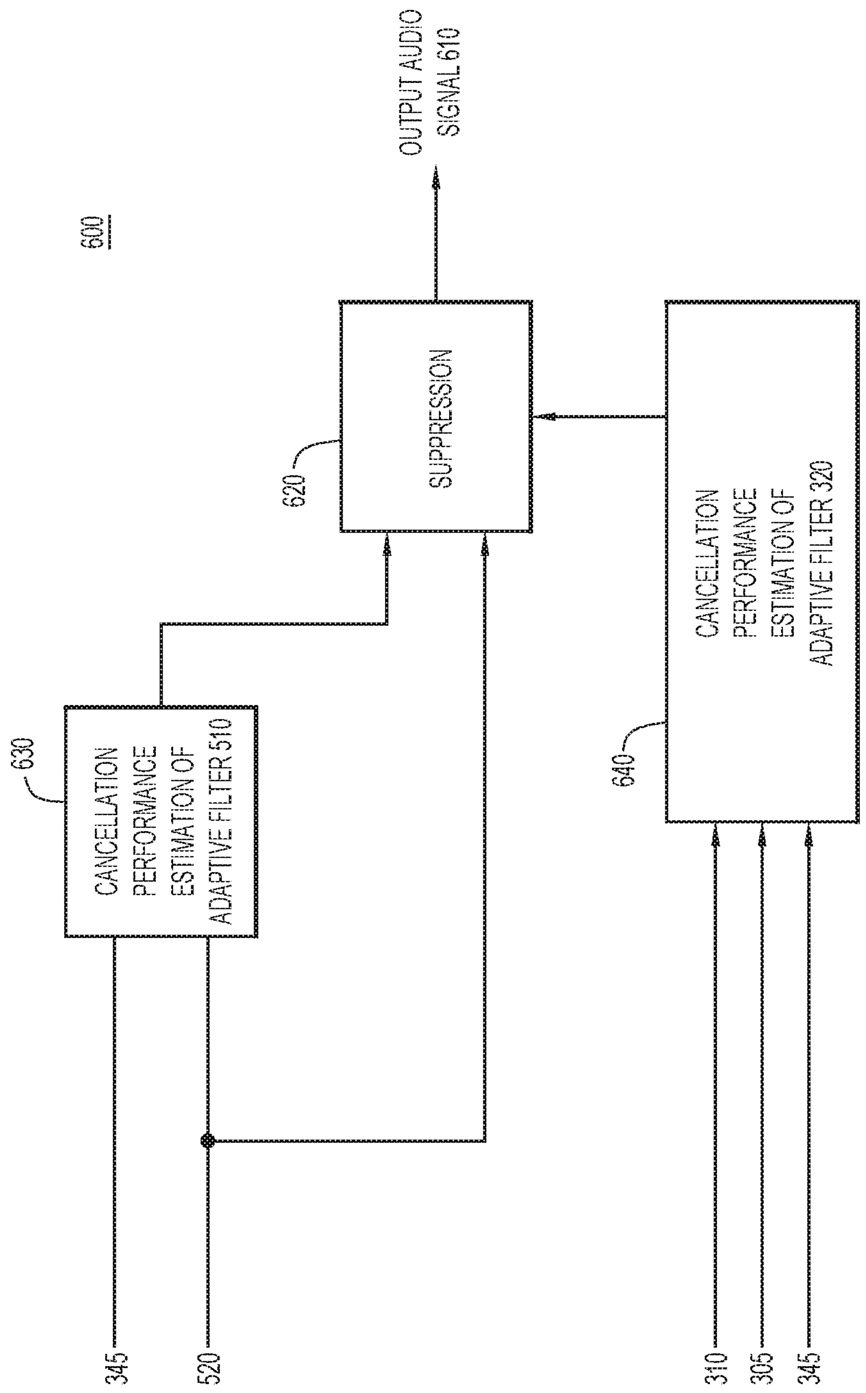
FIG. 6 is a functional signal processing flow diagram illustrating suppression of an anisotropic background audio signal, according to an example embodiment.

FIG. 6 is an example functional signal processing flow diagram 600 illustrating suppression of an anisotropic background audio signal. Reference is also made to FIGS. 1, 3, and 5 for purposes of the description of FIG. 6. In certain cases, fourth audio signal 520 may still include a remaining anisotropic background audio signal (e.g., residual from anisotropic background audio signal 155). To fully remove anisotropic background audio signal 155 from output audio signal 610, the anisotropic background audio signal control logic 160 may include a suppression function 620 that performs noise suppression on the fourth audio signal 520. Suppression function 620 may calculate (e.g., in the frequency domain) a suppression gain for the fourth audio signal 520 based on the user audio signal and anisotropic background audio signal 155. More specifically, suppression function 620 may calculate the suppression gain based on an estimated signal strength of the user audio signal, an estimated signal strength of anisotropic background audio signal 155, and cancellation performance of anisotropic background audio signal 155 to produce output audio signal 610. Suppression function 620 may produce output audio signal 610 by applying the suppression gain to the fourth audio signal 520, thereby removing any remaining anisotropic background audio signal. Headset 115(1) may provide output audio signal 610 to a receiver device (e.g., telephony device 120(1), which in turn communicates to telephony device 120(2) via communications server 110)).

Suppression function 620 may determine the estimated signal strength of the user audio signal by comparing the signal strengths between reference signal 305 and the third audio signal 345. In particular, the third audio signal 345 includes the user audio signal, anisotropic background audio signal 155, and any (isotropic) background/environmental noise, while reference signal 305 includes anisotropic background audio signal 155 and the (isotropic) background/environmental noise, with the user audio signal removed. Moreover, suppression function 620 may use the SNR of reference signal 305 as the estimated signal strength of anisotropic background audio signal 155.

Performance estimation function 630 may provide a performance estimation of adaptive filter 510, and performance estimation function 640 may provide a performance estimation of adaptive filter 320. If there is strong performance from adaptive filter 320 (as indicated by performance estimation node 640), a user audio signal may be present, and therefore suppression may be limited (or nonexistent) so as to avoid distorting the user audio signal. For example, if there is a strong user audio signal, the first audio signal 310 and the third audio signal 345 would be relatively high, and reference signal 305 would be relatively low. Meanwhile, a strong performance from adaptive filter 510 (as indicated by performance estimation function 630) indicates that adaptive filter 510 is cancelling a large quantity of anisotropic background audio signal 155, and therefore suppression may be warranted. For example, when the estimated signal strength of the user audio signal is low, performance estimation function 630 may determine the cancellation performance of anisotropic background audio signal 155 by comparing the respective signal strengths of the third audio signal 345 and the fourth audio signal 520. With anisotropic background audio signal 155 removed from the third audio signal 345, the fourth audio signal 520 has the user audio signal and environmental noise. When meeting attendee 105(1) is not talking (i.e., the estimated signal strength of the user audio signal is low), the fourth audio signal 520 is mainly environment noise.

When the estimated user audio signal strength is relatively low, the suppression gain should be low if the estimated signal strength of anisotropic background audio signal 155 is relatively high and there is strong cancellation performance of anisotropic background audio signal 155. Low suppression gain attenuates anisotropic background audio signal 155 residue in the fourth audio signal 520. When the estimated signal strength of the user audio signal is relatively high, the suppression gain should be calculated based on the mask effect of the user audio signal and anisotropic background audio signal 155. When the estimated signal strength of the user audio signal is much higher than that of anisotropic background audio signal 155, anisotropic background audio signal 155 is masked by the user audio signal, and as such the suppression gain may be relatively high. When the estimated signal strength of anisotropic background audio signal 155 is high relative to the estimated signal strength of the user audio signal, more attenuation is necessary, and therefore the suppression gain should be relatively low.

The suppression gain calculation may consider both global spectrum (for all frequencies) and local spectrum (for specific frequency bins) of the user audio signal and the anisotropic background audio signal 155 signal strength. When global anisotropic background audio signal 155 signal strength is high, even if anisotropic background audio signal 155 signal strength is low for a specific frequency, gain for that frequency may be lower than it would otherwise be when the global anisotropic background audio signal 155 signal strength is low.

Figure 7:
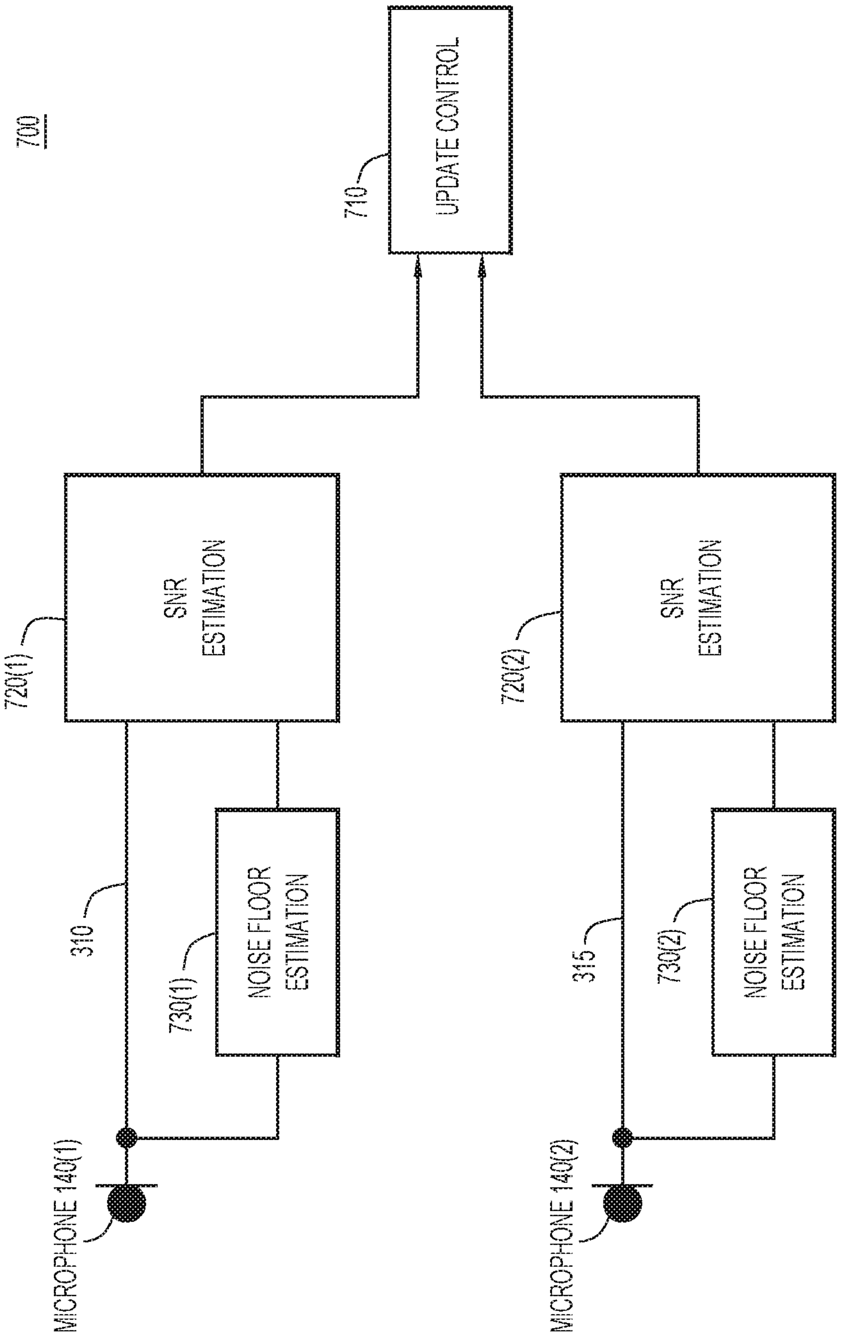
FIG. 7 is a functional signal processing flow diagram illustrating update control of an adaptive filter configured to extract a reference signal, according to an example embodiment.

FIG. 7 is an example functional signal processing flow diagram 700 illustrating update control of adaptive filter 320. Reference is also made to FIGS. 1 and 3 for purposes of the description of FIG. 7. The anisotropic background audio signal control logic 160 may include update control function 710, which controls coefficient updates to adaptive filter 320 based on SNR estimations 720(1) and 720(2) associated with first and second audio signals 310 and 315. SNR estimations 720(1) and 720(2) may be based on noise floor estimations 730(1) and 730(2) of first and second audio signals 310 and 315, respectively. Adaptive filter 320 may have a very fast convergence time with a short tail length. Since the relative distances between microphones 140(1) and 140(2) and the mouth of meeting attendee 105(1) is fairly constant, adaptive filter 320 need not update constantly/continuously. Update control function 710 may update coefficients of adaptive filter 320 when the SNR of first audio signal 310 is greater than a first predefined threshold, and when the SNR of second audio signal 315 is greater than a second predefined threshold. In one example, the predefined thresholds are set such that adaptive filter 320 is only updated when meeting attendee 105(1) is speaking.

Figure 8:
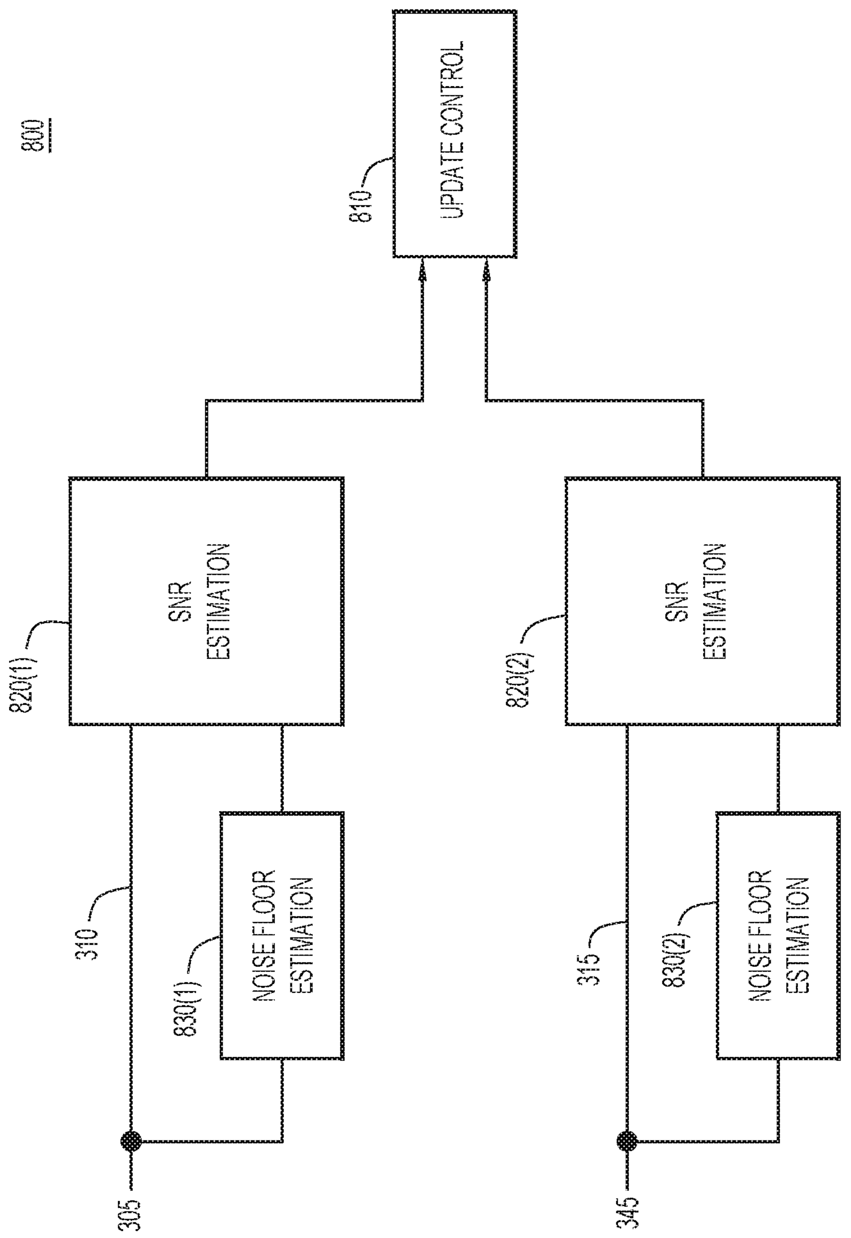
FIG. 8 is a functional signal processing flow diagram illustrating update control of an adaptive filter configured to cancel an anisotropic background audio signal, according to an example embodiment.

FIG. 8 is an example functional signal processing flow diagram 800 illustrating update control of adaptive filter 510. Reference is also made to FIGS. 1, 3, and 5 for purposes of the description of FIG. 8. The anisotropic background audio signal control logic 160 may include update control function 810, which controls coefficient updates to adaptive filter 510 based on SNR estimations 820(1) and 820(2) of reference signal 305 and the third audio signal 345. SNR estimations 820(1) and 820(2) may be based on noise floor estimations 830(1) and 830(2) of reference signal 305 and the third audio signal 345, respectively. Adaptive filter 510 may update when the SNR of reference signal 305 is greater than a third predefined threshold, and when the SNR of the third audio signal 345 is between a fourth predefined threshold and a fifth predefined threshold. When both the user audio signal and anisotropic background audio signal 155 are present simultaneously, the third audio signal 345 may have a higher strength than reference signal 305. In this case, the fourth audio signal 520 is relatively large, and update control function 810 may cease coefficient updating.

Figure 9:
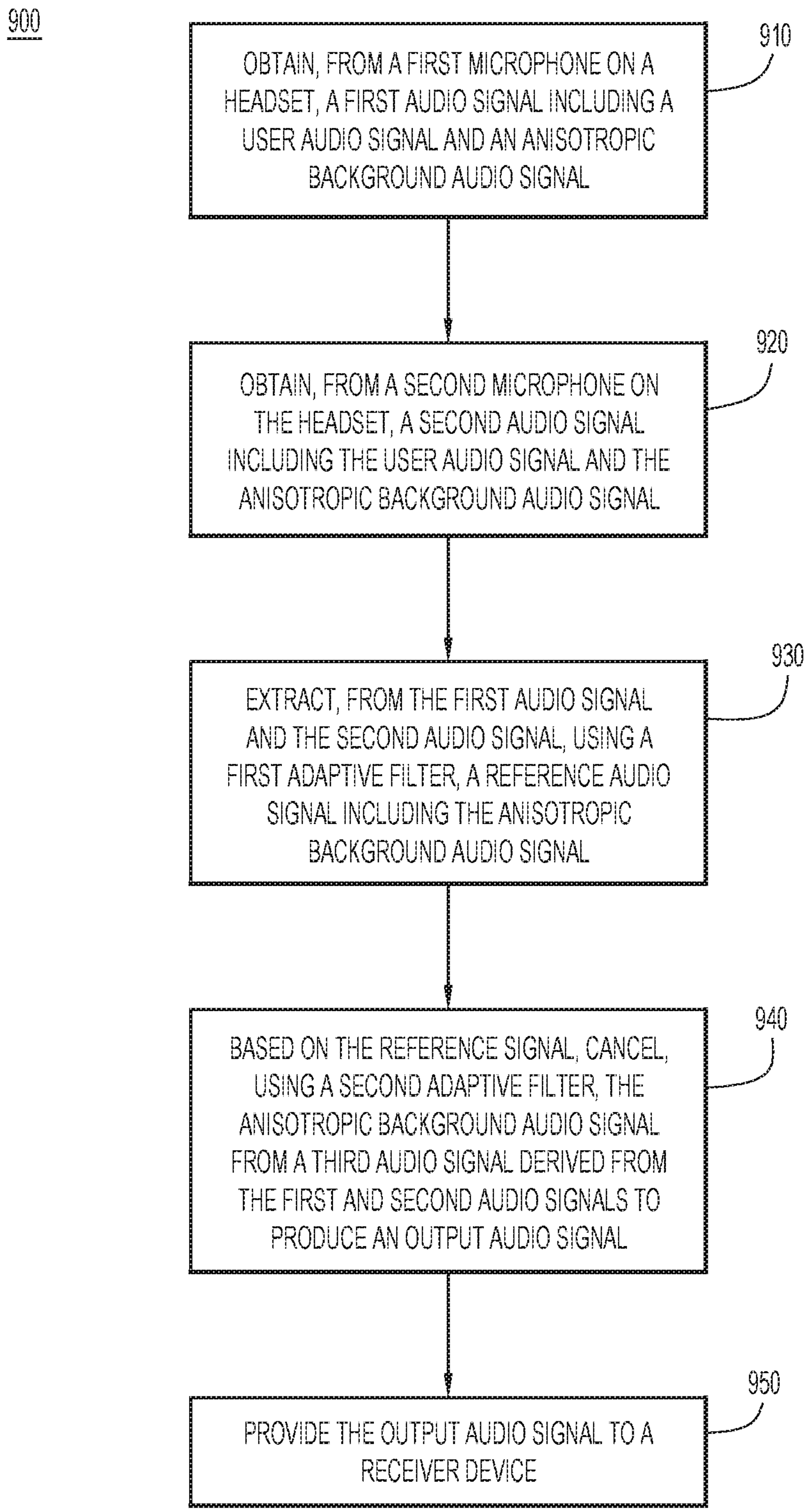
FIG. 9 is a flowchart of a method for controlling an anisotropic background audio signal, according to an example embodiment.

FIG. 9 is a flowchart of an example method 900 for controlling an anisotropic background audio signal. Reference is made to FIG. 1 for purposes of the description of FIG. 9. Method 900 may be performed by headset 115(1). At 910, headset 115(1) obtains, from a first microphone on a headset, a first audio signal including a user audio signal and an anisotropic background audio signal. At 920, headset 115(1) obtains, from a second microphone on the headset, a second audio signal including the user audio signal and the anisotropic background audio signal. At 930, headset 115(1) extracts, from the first audio signal and the second audio signal, using a first adaptive filter, a reference audio signal including the anisotropic background audio signal. At 940, based on the reference signal, headset 115(1) cancels, using a second adaptive filter, the anisotropic background audio signal from a third audio signal derived from the first and second audio signals to produce an output audio signal. At 950, headset 115(1) provides the output audio signal to a receiver device.

Techniques are presented to remove an anisotropic background audio signal from a microphone audio signal before sending an output audio signal to remote side in a conference call. A method that combines anisotropic background audio signal cancellation and suppression may optimize the audio experience for headsets. Multiple microphones may be used in these methods. Two adaptive filters may be used: one for reference signal extraction, and the other for anisotropic background audio signal cancellation. Techniques described herein may apply in boom or boomless headsets.

In one form, an apparatus is provided. The apparatus comprises: a first microphone; a second microphone; and a processor coupled to receive signals derived from outputs of the first microphone and the second microphone, wherein the processor is configured to: obtain, from the first microphone, a first audio signal including a user audio signal and an anisotropic background audio signal; obtain, from the second microphone, a second audio signal including the user audio signal and the anisotropic background audio signal; extract, from the first audio signal and the second audio signal, using a first adaptive filter, a reference audio signal including the anisotropic background audio signal; based on the reference signal, cancel, using a second adaptive filter, the anisotropic background audio signal from a third audio signal derived from the first and/or second audio signals to produce an output audio signal; and provide the output audio signal to a receiver device.

In one example, the apparatus further comprises a first earpiece that houses the first microphone and a second earpiece that houses the second microphone. In a further example, the processor is further configured to: select the third audio signal from a plurality of candidate audio signals, wherein the plurality of candidate audio signals includes the first audio signal, the second audio signal, and the third audio signal. In a still further example, the processor is configured to select the third audio signal based on a signal-to-noise ratio of the first audio signal, a signal-to-noise ratio the second audio signal, and/or a signal-to-noise ratio of the combined signal. In another still further example, the processor is configured to select the third audio signal based on an envelope of the output of the first adaptive filter.

In one example, the apparatus further comprises: a boom that houses the first microphone and the second microphone, wherein the first microphone is a directional microphone oriented toward a source of the user audio signal. In a further example, the third audio signal is the first audio signal. In another further example, the second microphone is a directional microphone oriented away from the source of the user audio signal. In yet another further example, the second microphone is an omnidirectional microphone.

In one example, the processor is configured to cancel the anisotropic background audio signal to produce a fourth audio signal, and the processor is further configured to: calculate a suppression gain based on the user audio signal and the anisotropic background audio signal; and remove a remaining anisotropic background audio signal from the fourth audio signal by applying the suppression gain to the fourth audio signal to produce the output audio signal.

In one example, the processor is further configured to: update coefficients of the first adaptive filter when a signal-to-noise ratio of the first audio signal is greater than a first predefined threshold, and when a signal-to-noise ratio of the second audio signal is greater than a second predefined threshold.

In one example, the processor is further configured to: update coefficients of the second adaptive filter when a signal-to-noise ratio of the reference signal is greater than a first predefined threshold, and when a signal-to-noise ratio of the third audio signal is between a second predefined threshold and a third predefined threshold.

In one example, the processor is further configured to: delay the first audio signal by a length of time substantially equal to a difference between a time at which the user audio signal reaches one of the first microphone and the second microphone and a time at which the user audio signal reaches the other of the first microphone and the second microphone.

In another form, a method is provided. The method comprises: obtaining, from a first microphone on a headset, a first audio signal including a user audio signal and an anisotropic background audio signal; obtaining, from a second microphone on the headset, a second audio signal including the user audio signal and the anisotropic background audio signal; extracting, from the first audio signal and the second audio signal, using a first adaptive filter, a reference audio signal including the anisotropic background audio signal; based on the reference signal, cancelling, using a second adaptive filter, the anisotropic background audio signal from a third audio signal derived from the first and second audio signals to produce an output audio signal; and providing the output audio signal to a receiver device.

In another form, one or more non-transitory computer readable storage media are provided. The non-transitory computer readable storage media are encoded with instructions that, when executed by a processor, cause the processor to: obtain, from a first microphone on a headset, a first audio signal including a user audio signal and an anisotropic background audio signal; obtain, from a second microphone on the headset, a second audio signal including the user audio signal and the anisotropic background audio signal; extract, from the first audio signal and the second audio signal, using a first adaptive filter, a reference audio signal including the anisotropic background audio signal; based on the reference signal, cancel, using a second adaptive filter, the anisotropic background audio signal from a third audio signal derived from the first and second audio signals to produce an output audio signal; and provide the output audio signal to a receiver device.

The above description is intended by way of example only. Although the techniques are illustrated and described herein as embodied in one or more specific examples, it is nevertheless not intended to be limited to the details shown, since various modifications and structural changes may be made within the scope and range of equivalents of the claims.

What is claimed is:

1. An apparatus comprising:

a first microphone;

a second microphone; and a processor coupled to receive signals derived from outputs of the first microphone and the second microphone, wherein the processor is configured to:

obtain, from the first microphone, a first audio signal including a user audio signal and an anisotropic background audio signal;

obtain, from the second microphone, a second audio signal including the user audio signal and the anisotropic background audio signal;

extract, from the first audio signal and the second audio signal, using a first adaptive filter, a reference audio signal including the anisotropic background audio signal;

based on the reference audio signal, cancel, using a second adaptive filter, the anisotropic background audio signal from a third audio signal derived from the first and/or second audio signals to produce an output audio signal; and provide the output audio signal to a receiver device.

2. The apparatus of claim 1, further comprising:

a first earpiece that houses the first microphone and a second earpiece that houses the second microphone.

3. The apparatus of claim 2, wherein the processor is further configured to:

select the third audio signal from a plurality of candidate audio signals, wherein the plurality of candidate audio signals includes the first audio signal, the second audio signal, and the third audio signal.

4. The apparatus of claim 3, wherein the processor is configured to select the third audio signal based on a signal-to-noise ratio of the first audio signal, a signal-to-noise ratio of the second audio signal, and/or a signal-to-noise ratio of the third audio signal.

5. The apparatus of claim 3, wherein the processor is configured to select the third audio signal based on an envelope of the first adaptive filter.

6. The apparatus of claim 1, further comprising:

a boom that houses the first microphone and the second microphone, wherein the first microphone is a directional microphone oriented toward a source of the user audio signal.

7. The apparatus of claim 6, wherein the third audio signal is the first audio signal.

8. The apparatus of claim 6, wherein the second microphone is a directional microphone oriented away from the source of the user audio signal.

9. The apparatus of claim 6, wherein the second microphone is an omnidirectional microphone.

10. The apparatus of claim 1, wherein the processor is configured to cancel the anisotropic background audio signal to produce a fourth audio signal, and wherein the processor is further configured to:

calculate a suppression gain based on the user audio signal and the anisotropic background audio signal; and remove a remaining anisotropic background audio signal from the fourth audio signal by applying the suppression gain to the fourth audio signal to produce the output audio signal.

11. The apparatus of claim 1, wherein the processor is further configured to:

update coefficients of the first adaptive filter when a signal-to-noise ratio of the first audio signal is greater than a first predefined threshold, and when a signal-to-noise ratio of the second audio signal is greater than a second predefined threshold.

12. The apparatus of claim 1, wherein the processor is further configured to:

update coefficients of the second adaptive filter when a signal-to-noise ratio of the reference audio signal is greater than a first predefined threshold, and when a signal-to-noise ratio of the third audio signal is between a second predefined threshold and a third predefined threshold.

13. The apparatus of claim 1, wherein the processor is further configured to:

delay the first audio signal by a length of time substantially equal to a difference between a time at which the user audio signal reaches one of the first microphone and the second microphone and a time at which the user audio signal reaches the other of the first microphone and the second microphone.

14. A method comprising:

obtaining, from a first microphone on a headset, a first audio signal including a user audio signal and an anisotropic background audio signal;

obtaining, from a second microphone on the headset, a second audio signal including the user audio signal and the anisotropic background audio signal;

extracting, from the first audio signal and the second audio signal, using a first adaptive filter, a reference audio signal including the anisotropic background audio signal;

based on the reference audio signal, cancelling, using a second adaptive filter, the anisotropic background audio signal from a third audio signal derived from the first and second audio signals to produce an output audio signal; and providing the output audio signal to a receiver device.

15. The method of claim 14, wherein cancelling the anisotropic background audio signal produces a fourth audio signal, the method further comprising:

calculating a suppression gain based on the user audio signal and the anisotropic background audio signal; and removing a remaining anisotropic background audio signal from the fourth audio signal by applying the suppression gain to the fourth audio signal to produce the output audio signal.

16. The method of claim 14, further comprising:

updating coefficients of the first adaptive filter when a signal-to-noise ratio of the first audio signal is greater than a first predefined threshold, and when a signal-to-noise ratio of the second audio signal is greater than a second predefined threshold.

17. The method of claim 14, further comprising:

updating coefficients of the second adaptive filter when a signal-to-noise ratio of the reference audio signal is greater than a first predefined threshold, and when a signal-to-noise ratio of the third audio signal is between a second predefined threshold and a third predefined threshold.

18. One or more non-transitory computer readable storage media encoded with instructions that, when executed by a processor, cause the processor to:

obtain, from a first microphone on a headset, a first audio signal including a user audio signal and an anisotropic background audio signal;

obtain, from a second microphone on the headset, a second audio signal including the user audio signal and the anisotropic background audio signal;

extract, from the first audio signal and the second audio signal, using a first adaptive filter, a reference audio signal including the anisotropic background audio signal;

based on the reference audio signal, cancel, using a second adaptive filter, the anisotropic background audio signal from a third audio signal derived from the first and second audio signals to produce an output audio signal; and provide the output audio signal to a receiver device.

19. The one or more non-transitory computer readable storage media of claim 18, wherein cancelling the anisotropic background audio signal produces a fourth audio signal, and wherein the instructions further cause the processor to:

calculate a suppression gain based on the user audio signal and the anisotropic background audio signal; and remove a remaining anisotropic background audio signal from the fourth audio signal by applying the suppression gain to the fourth audio signal to produce the output audio signal.

20. The one or more non-transitory computer readable storage media of claim 18, wherein the instructions further cause the processor to:

update coefficients of the first adaptive filter when a signal-to-noise ratio of the first audio signal is greater than a first predefined threshold, and when a signal-to-noise ratio of the second audio signal is greater than a second predefined threshold.

* * * * *